United States Patent [19]

Dewing et al.

[11] Patent Number: 4,677,239
[45] Date of Patent: Jun. 30, 1987

[54] TOLUENE DISPROPORTIONATION WITH A SURFACE DEALUMINATED ZEOLITE

[75] Inventors: John Dewing, Chester; Philip J. Hogan; Allan Stewart, both of Cheshire, all of England

[73] Assignee: Imperial Chemical Industries PLC, London, England

[21] Appl. No.: 702,613

[22] Filed: Feb. 19, 1985

Related U.S. Application Data

[62] Division of Ser. No. 497,227, May 23, 1983, Pat. No. 4,533,533.

[30] Foreign Application Priority Data

May 27, 1982 [GB] United Kingdom ................ 8215531

[51] Int. Cl.$^4$ ................................................ C07C 5/52
[52] U.S. Cl. ..................................... 585/475; 585/470
[58] Field of Search ............... 585/475, 470; 423/328; 502/69, 71, 77

[56] References Cited

U.S. PATENT DOCUMENTS

| | | | |
|---|---|---|---|
| 4,127,616 | 11/1978 | Rodewald | 585/475 |
| 4,148,713 | 4/1979 | Rollmann | 585/475 |
| 4,533,533 | 8/1985 | Dewing et al. | 502/60 |

Primary Examiner—John Doll
Assistant Examiner—Lance Johnson
Attorney, Agent, or Firm—Cushman, Darby & Cushman

[57] ABSTRACT

Selective and controlled dealumination of an aluminosilicate zeolite is achieved by filling the pore system of the zeolite with a foreign material, for example coke, removing part of the foreign material from the outer portion of the zeolite, for example by heating in a gas stream comprising oxygen, dealuminating the outer portion, and then removing the remainder of the foreign material. Use of such a partially dealuminated zeolite as catalyst in a toluene disproportionation reaction leads to greater selectivity to paraxylene.

3 Claims, No Drawings

TOLUENE DISPROPORTIONATION WITH A SURFACE DEALUMINATED ZEOLITE

This is a division of application Ser. No. 497,227, filed May 23, 1983, now U.S. Pat. No. 4,533,533.

The present invention relates to a method for the preparation of modified zeolites and to their use as catalysts in hydrocarbon processes.

Zeolites have been known for very many years but interest in their use as molecular sieves and as catalysts has increased very considerably over the last 30 years. Many zeolites occur in nature and in recent years many synthetic zeolites have also been prepared. The technical literature of the last 25 years or so is replete with descriptions of new zeolites and of their preparation and with proposals for the use of zeolites, both old and new, as catalysts in a wide variety of chemical processes. Many of these proposals relate to the use of zeolites in processes used in the oil and petrochemical industry such as aromatisation, hydrocarbon cracking, isomerisation processes and the like.

Some zeolite materials are ordered, porous, crystalline aluminosilicates having a crystalline structure in which there is a large number of smaller cavities which may be interconnected by a number of even smaller channels. These cavities and channels are uniform in size and their dimensions impart the useful property of being able to absorb molecules of certain dimensions while rejecting molecules of larger dimensions.

Zeolites both natural and synthetic, include a considerable number of cation-containing crystalline aluminosilicates which can be characterised as rigid three-dimensional frameworks of $SiO_4$ and $AlO_4$ in which the tetrahedra are cross-linked by the sharing of oxygen atoms whereby the ratio of the total aluminium and silicon atoms to oxygen is 1:2. The electrovalence of the tetrahedra containing aluminium is balanced by the inclusion in the crystal of a suitable cation. The properties of a given cation-containing aluminosilicate zeolite can be varied by suitable selection of a cation and it is now common practice to ion-exchange one cation for another, either partially or completely, so as to obtain a zeolite most suited for the particular purpose presently in mind.

Natural zeolites have generally been given generic names, for example faujasite, mordenite, while synthetic zeolites are usually designated by letter or other convenient symbols, for example zeolites A, X, Y, FU-1, Nu-1, ZSM-5 etc.

Besides the presence or absence of certain cations, another factor which is known to influence the properties of a zeolite is its structural silica to alumina mole ratio. For example, it has been noted that such properties as catalytic activity, thermal stability and resistance to acid and steam attack can all be influenced by an increase in the silica-to-alumina mole ratio of a zeolite. In synthetic zeolites this ratio is essentially determined by the nature and relative quantities of the starting materials used to prepare the zeolite. Some variations in the silica/alumina mole ratio can be obtained by changing the proportion of the reactants for example by increasing the amount of silica precursor, but it has been observed that beyond a certain point changing the proportions of the reactants has no effect on the silica/alumina mole ratio.

Thus, a number of alternative methods have been proposed in order to obtain zeolites having desirably higher silica/alumina mole ratios. For example, aluminium has been removed from the crystal structure using strong acids. In another method, described in U.S. Pat. No. 3,691,099, an aluminosilicate was treated with a mild acid solution containing at least one water soluble salt of an exhangeable cation for sufficient time and at a sufficient temperature to remove structural aluminium from the aluminosilicate structure. Another method is described in U.S. Pat. No. 3,640,681 in which framework aluminium is extracted from a crystalline zeolite using acetylacetone as extractant. A paper by Fejes et al in Reaction Kinetics and Catalysis Letters Vol 14, (No. 4), 481 (1980) describes how a wide range of halogen-containing reagents, for example metal halides, oxyhalides, acid halides interact from the gas phase with exchange ions of H-mordenite to effect dealumination of the zeolite at elevated temperatures. In another paper by Beyer et al in "Catalysis by Zeolites" ed. B. Imelik et al (Elsevier Scientific Publishing Co., Amsterdam, 1980) page 203 et. seq, a method is described for dealuminating Y-type zeolites by reaction with silicon tetrachloride. In U.S. Pat. No. 4,273,753 a process is described for removing aluminium from crystallization zeolites by contacting the zeolite with an inorganic halide or oxyhalide at a temperature sufficiently high to volatilise the aluminium halide or oxyhalide which is formed, The inorganic halide is, for example, silicon tetrachloride.

According to the present invention a process for the controlled removal of aluminium from a crystalline aluminosilicate zeolite comprises:

(a) subjecting the zeolite to a treatment whereby the pore system of the zeolite is filled substantially completely with a foreign material;

(b) selectively removing a portion of said foreign material from an outer zone of the zeolite crystal structure;

(c) contacting the zeolite from step (b) with a dealuminating agent to which the said foreign material is substantially inert under the process conditions for a sufficient time and under suitable process conditions as to remove at least some of the aluminium from the zeolite; and (d) subjecting the thus partially de-aluminated zeolite to further treatment whereby to remove substantially the remainder of said foreign material.

In one preferred embodiment of this invention, steps (a) to (d) of the process are carried out sequentially but if desired steps (b) and (c) may be carried out simultaneously.

Foreign materials for filling the pore system of the zeolite comprise any material which is (i) inert to the dealuminating agent used in step (c) of the process and (ii) readily removable itself from the pores of the zeolite. Preferred foreign materials include (a) carbonaceous residues generally known in the petrochemical art as "coke", (b) organic materials including, for example oligomers and polymers, for example polystyrene or oligomers of styrene, quaternary ammonium cations especially those used in zeolite synthesis, for example tetrapropyl ammmonium cations, and (c) materials substantially immiscible with the dealuminating agent or the medium in which the dealuminating agent is used. Suitably the said substantially immiscible material comprises a liquid hydrocarbon, for example octane or toluene.

A preferred embodiment of the process of this invention comprises:

(a) subjecting a zeolite to a coking treatment in which a carbonaceous residue ("coke") is deposited throughout the zeolite crystal to a degree which substantially completely blocks access to the zeolite pore structure;

(b) selectively de-coking the coked zeolite whereby to partially remove the coke deposited in step (a);

(c) contacting the partially de-coked zeolite with a dealuminating agent for a sufficient time and under suitable process conditions as to remove at least some of the aluminium from the zeolite; and (d) subjecting the zeolite to further de-coking whereby to produce a dealuminated zeolite substantially free of coke.

Catalyst coking is a well-known phenomonen which operators of catalytic processes usually prefer to avoid, if at all possible. It occurs in many processes, especially hydrocarbon conversion processes, and leads to a gradual worsening of the performance of the catalyst until eventually the catalyst has to be regenerated ("de-coked"), usually by burning off the coke at elevated temperature in an oxidising atmosphere.

The Applicants have now surprisingly found that a preliminary coking of a zeolite, followed by partial de-coking, allows selective dealumination of the zeolite to be achieved. As a result, a zeolite is produced which, it is believed, has an inner core of unaffected aluminosilicate material and an outer skin which, although retaining the zeolite crystalline structure, contains a reduced amount of, or even no, aluminium.

The coking in step (a) of this embodiment of the process may be effected by passage of a stream of a coking agent over the zeolite at elevated temperature, say at greater than 300° C. and typically at greater than 450° C. The coking agent may be any one or more of a range of carbonaceous materials, for example alcohols and hydrocarbons. These include alkenes and aromatic hydrocarbons, for example propene, isobutene, toluene and ortho-xylene. The coking is carried out for a sufficient time to completely coke the zeolite and completion of coking can be ascertained by analysing samples of the zeolite.

The de-coking in step (b) of this embodiment is preferably carried out in the presence of a gas stream comprising oxygen, conveniently an air stream, at elevated temperature, for example at a temperature in the range 450° C. to 650° C. The de-coking is carried out for a sufficient time so at least some of the coke is left untouched within the zeolite structure. The amount of de-coking required is a matter of choice for the operator depending on the type of performance required from the eventually-dealuminated zeolite. However those skilled in this art should be able readily to determine the extent of de-coking for their own particular catalytic requirements. The final de-coking of step (d) is carried out in the same way as that of step (b) until substantially all the coke has been removed from the zeolite.

A further embodiment of the process of this invention comprises:

(a) selecting a zeolite containing organic material within at least part of its pore system and, if necessary, treating said zeolite with further organic material whereby to substantially fill said zeolite pore system with organic material;

(b) selectively removing a portion of said organic material from an outer zone of the zeolite crystal structure;

(c) contacting the zeolite product from step (b) with a dealuminating agent whereby to remove at least some of the aluminium from the zeolite; and (d) subjecting the zeolite product from step (c) to treatment to remove substantially completely remaining organic material from the pore system of said zeolite.

In a preferred form of this embodiment the organic material comprises material used in the synthesis of the zeolite for example quaternary ammonium cations. In this preferred form the organic material may be removed from the outer zone of the zeolite (step (b)) by controlled oxidation at elevated temperatures followed, if necessary, by treatment to render the aluminium in the framework of said outer zone susceptible to attack by the dealuminating agent used in step (c), for example by exchange of any metallic cations other than aluminium and silicon by protons.

The dealumination in step (c) of the process of this invention may be carried out using any one or more of a number of dealuminating agents. Suitable agents include metal halides, oxyhalides, acid halides, for example silicon tetrachloride, phosgene, thionyl chloride; complexing agents for example ethylenediamine tetraacetic acid; acids for example hydrochloric acid; steam; and halogens for example chlorine and fluorine. The choice of dealuminating agent and the conditions of dealumination are decided to some extent by the nature of the foreign material in the zeolite. Thus, for example, the dealuminating agent should not be one which requires the dealumination to be carried out at a temperatue which is so high that the foreign material becomes unstable or decomposes except, in this instance, where stages (b) and (c) can be advantageously combined. In some cases, it may be desirable to select a dealuminating agent of such a size that it penetrates only slowly into the zeolite crystallite. In some such cases this desired diffusional restriction may be more readily achieved by using the zeolite in a cationic or partially coked form where the cations or coke retards the diffusion rate of the agent.

Throughout the process of this invention, it is important that the conditions chosen should not be so severe that the crystallinity of the zeolite is adversely affected.

Optionally, between steps (b) and (c) of the process, metallic cations other than aluminium which may be present in the zeolite may be partially or completely removed by conventional methods, for example by ion-exchange. In practice, as the inner core of the zeolite at this stage will still be filled with foreign material, for example coke, this means that only those metallic cations present in the outer skin will be susceptible to removal. However, if desired, removal of the remainder of the metallic cations may be carried out after step (d).

If desired, following step (d) of the process of the invention the zeolite may be acid-washed, for example with dilute mineral acid.

The process of this invention produces a crystalline zeolite in which the crystalline structure is substantially retained and which, it is believed, comprises an inner core of aluminosilicate material having a silica to alumina mole ratio substantially unaffected by the process and an outer skin which has been at least partially dealuminated and which therefore has a higher silica to alumina mole ratio. In effect a selective diffusional barrier has depth of several hundred Angstroms renders this part of the crystal inactive in disproportionation and isomerisation, thus decreasing the possibility of m-xylene and o-xylene escaping from the crystals without markedly affecting the escape of p-xylene. The p-xylene cannot readily isomerise back to m- and o-xylenes in the dealuminated zone and so the production of the para isomer is enhanced. The zeolite catalyst can be visualised as consisting of an inner, catalytically active core, and an outer, catalytically inactive skin acting as a molecular sieve.

It is considered that the process of this invention can be used to improve the performance of a wide variety of zeolite catalysts, for example mordenites, ferrierites, FU-1, FU-9, Nu-1, Nu-2, Nu-3, Nu-4, Nu-5, Nu-6, Nu-10, EU-1, EU-2, EU-4, ZSM-5, 11, 12, 35, 38 and 48. Descriptions of the characteristics of each of these zeolites have been given in a number of prior art specifications of which the following references are typical:

FU-1: U.K. Pat. No. 1,563,346
FU-9: European Patent Application No. 55,529
Nu-1: U.K. Pat. No. 1,556,367
Nu-2: European Patent Application No. 55046
Nu-3: European Patent Application No. 40016
Nu-4: European Patent Application No. 65,401
Nu-5: European Patent Application No. 54386
Nu-6: European Patent Application No. 54364
Nu-10: European Patent Application No. 65400
EU-1: European Patent Application No. 42226
EU-2: U.K. Pat. No. 2,077,709
EU-4: European Patent Application No. 63436
ZSM-5: U.S. Pat. No. 3,702,886
ZSM-11: U.S. Pat. No. 3,709,979
ZSM-12: U.S. Pat. No. 3,832,449
ZSM-35: U.S. Pat. No. 4,016,245
ZSM-38: U.S. Pat. No. 4,046,859
ZSM-48: European Patent Application No. 23089

As is known, zeolite catalysts are suitable for use in catalysing many hydrocarbon conversion processes, for example cracking, hydrocracking, hydrogenation, dehydrogenation, reforming, aromatisation, alkylation, disproportionation and isomerisation reactions and it is expected that zeolites prepared by the method of this invention will be suitable for use in such hydrocarbon conversions. For example, the Applicants have found that zeolites prepared according to the method of this invention provide improved perfromances in the disproportionation of toluene to benzene and xylene and the methylation of toluene to form xylenes. Further it is believed that a possibly higher yield of aromatic or higher aliphatic hydrocarbons will be obtainable in the conversion of methanol coupled with a reduction in aromatic "heavy ends".

The invention is further illustrated by the following examples in which Examples 1 and 2 illustrate the invention itself and Examples A, B and C are provided as comparative examples of prior art processes.

EXAMPLE A

Dealumination of zeolite H-ZSM-5

The sodium tetrapropylammonium form of zeolite ZSM-5 was prepared in conventional manner and was then converted to the acid form by calcination at 450° C. for 3 days followed by ion exchange using M/10 hydrochloric acid solution. This material was then dried at 100° C. for 3 hours. The silica-to-alumina ratio of the thus prepared material was found to be approximately 85:1.

The thus-prepared HZSM-5 (2.0 g) was heated and held at 600° C. in a flow of dry nitrogen for a short time. Thionyl chloride was then entrained in a stream of 50 ml/min nitrogen by bubbling the gas through a vessel containing the thionyl chloride and this stream was passed over the zeolite for 4.5 hours during which time the temperature was raised to and held mostly at 600° C. A total of 4 cm$^3$ of thionyl chloride was passed into zeolite during that time. When the zeolite was initially contacted with the thionyl chloride vapour, an exothermic reaction was noted and the temperature rose above 600° C. for a short period. The treated zeolite was cooled in nitrogen and washed thoroughly with deionised water before drying overnight at 90° C. Analysis of the resulting treated zeolite showed a silica to alumina ratio of approximately 595, i.e. a very substantial decrease in the aluminium content had occurred as the result of the dealumination treatment.

EXAMPLE B

Toluene disproportionation with HZSM-5

Some of the acid form of ZSM-5, prepared as described in the first paragraph of Example A, was compressed, crushed and sieved. 0.4123 g of HZSM-5 in the particle size range 250–500$\mu$ were loaded into a microreactor and heated up to 529° C. in nitrogen.

Toluene, fed by a peristaltic pump, was vaporised and the vapour passed over the zeolite in the microreactor at a rate equivalent to a weight hourly space velocity (WHSV) of 11.3. The results of this experiment are given in Table 1 below, and indicate a slight increase in selectivity to p-xylene in the xylenes fraction as the catalyst activity decays.

TABLE 1

| Time on line (hours) | Toluene Conversion (Mol %) | % p-xylene in xylenes fraction |
|---|---|---|
| 0.2 | 40.6 | 23.4 |
| 8.5 | 8.2 | 27.7 |
| 10.0 | 5.8 | 29.7 |
| 17.0 | 3.4 | 32.9 |
| 25.0 | 1.9 | 37.5 |

EXAMPLE C

Toluene disporportionation with "Dealuminated ZSM-5"

Some of the zeolite ZSM-5 prepared and dealuminated as described in Example A was pressed, crushed and sieved. 0.503 g of zeolite in the particle size range 250–500 were tested for toluene disproportionation in a similar manner to that described in Example B, except that the reaction temperature was 535° C. and the WHSV was 9.4. The results on the modified catalyst are given in Table 2 below.

TABLE 2

| Time on line (hours) | Toluene Conversion (Mol %) | % p-xylene in xylene fraction |
|---|---|---|
| 0.2 | 5.7 | 27.4 |
| 4.5 | 3.1 | 30.2 |
| 6.5 | 2.8 | 31.2 |

These results demonstrate a very low initial activity and no improvement in selectivity to p-xylene in the xylenes fraction at a given toluene conversion when compared to the data in Example B. Thus the conventional dealumination procedure employed in the modificatation of this catalyst has substantially reduced its activity without improving selectivity to p-xylene.

EXAMPLE 1

Selective dealumination of HZSM-5

About 2 g of zeolite HZSM-5 prepared as described in the first paragraph of Example A was "coked up" before treatment with thionyl chloride. The HZSM-5 sample was contacted with toluene at 515° C. by passing nitrogen at a flow rate of about 100 ml/min through a bubbler containing toluene and then over the zeolite. In 8 hours of such a treatment, about 6.5 cm$^3$ toluene was passed over the zeolite. The thus-treated sample of zeolite was then exposed to a nitrogen stream containing methanol vapour which was entrained in the nitrogen by again passing it through a bubbler. This treatment with methanol continued at 515° C. for 46 hours, during which time 69 cm$^3$ of methanol were passed. Elemental analysis of the zeolite, treated both with toluene and methanol, showed it to contain about 14% C and 40.3% Si. The zeolite was now black in appearance.

The dealumination was conducted in the presence of air so that dealumination and "de-coking" were taking place at the same time. (The Applicants believe that dealumination can take place only where coke has been removed from the zeolite pore system by combustion and the acid sites exposed to dealuminising agent.) Air was passed at 50 ml/min through a bubbler containing thionyl chloride and then over the "coked" zeolite at an initial temperature of 515° C. Due to an exothermic reaction the temperature rose above 515° C. but rapidly settled again at about 515° C. The time of treatment with the mixture of air and thionyl chloride was 1.75 hour and in that time 4 cm$^3$ of thionyl chloride were passed. The stream was then switched to nitrogen only and the treated zeolite sample was cooled. The treated zeolite was still black and was washed with de-ionised water and dried at 80° C. for 2 hours. Elemental analysis showed 5.94% C and 40.6% Si in this dried material and a Silica-to-Alumina ratio of about 99.

Prior to use as the catalyst in toluene disproportionation reactions the thus treated zeolite was calcined in air at 450° C. for 2 days to effect the final de-coking and produce the active catalyst.

The calcined zeolite together with samples of the acid form of ZSM-5, prepared as described in the first paragraph of example A, and of the "dealuminated ZSM-5", prepared as described in the second paragraph of Example A, were subjected to analysis by XPS (X-ray Photoelectron Spectroscopy) combined with an argon ion etch.

The original samples were analysed by XPS and were then analysed again after successive 20-minute etchings up to a total of 80 minutes. The rate of penetration was about 3 Å/minute so that the total depth of crystal penetrated after this 80 minute period was about 240 Å. The results of the analysis expressed as Si/Al atomic ratios, for the three samples are shown in Table 3.

TABLE 3

|  | Acid form ZSM-5 (Example A) | "Dealuminated ZSM-5" (Example A) | Selectively dealuminated ZSM-5 (Example 1) |
|---|---|---|---|
| Original sample | 32:1 | not measured | 59.5:1 |
| After 20 minute etch | 21:1 | 57:1 | 50:1 |
| After 40 minute etch | 18:1 | 47:1 | 40:1 |
| After 60 minute etch | 18:1 | 42:1 | 30:1 |
| After 80 minute etch | 17.5:1 | 28:1 | 25:1 |

The results for the acid form ZSM-5 show a relatively uniform distribution of aluminium while those for the "dealuminated ZSM-5" show an appreciable aluminium content near the surface. The results for the latter sample coupled with the fact that its silica/alumina mole ratio is very high (595:1) means that there is very little aluminium in the inner portion (below 240 Å from the surface) of the crystal. In contrast, the results for the selectively dealuminated sample show that the surface of the crystal has been depleted in aluminium relative to the original sample but that there is still a signifiant amount of aluminium in the inner portion, below 240 Å. These conclusions suggest that in a reaction such as toluene disproportionation the xylenes isomerisation rate relative to the rate of disproportionation should be substantially reduced for the selectively dealuminated ZSM-5 compared with the other two catalysts. The results obtained in Examples B and C and in Example 2 (see below) bear this out.

EXAMPLE 2

Toluene disproportionation with selectively dealuminated ZSM-5

Some of the zeolite prepared and modified according to the method of this invention, as described in Example 1, was pressed, crushed and sieved. 0.503 g of zeolite in the particle size range of 250–500μ were tested for toluene disproportionation in a similar manner to that described in Example B, except that the reaction temperature was 535° C. and the WHSV was 9.5. The results are given in Table 4 below.

TABLE 4

| Time on line (hours) | Toluene Conversion (Mol %) | % p-xylene in xylene fraction |
|---|---|---|
| 0.1 | 47.6 | 23.5 |
| 17.0 | 9.4 | 34.5 |
| 23.0 | 6.7 | 39.0 |
| 38.5 | 3.1 | 48.5 |
| 59.0 | 2.2 | 58.4 |

These results which are illustrated graphically in FIG. 1 demonstrate higher selectivity to p-xylene than found with the unmodified HZSM-5 (Example B) or the conventionally dealuminated ZSM-5 (Example C). In comparison with the unmodified HZSM-5 (Example B) the initial conversion has not been reduced unlike the case of the conventionally dealuminated ZSM-5 (Example C). At lower conversions brought about by catalytic deactivation, the selectivity to p-xylene in the xylenes fraction is substantially higher in this present Example than found at similar toluene conversion with the unmodified HZSM-5 (Example B).

What is claimed is:

1. A process for the disproportionation of toluene to benzene and xylene which comprises reacting toluene under disproportionation conditions using a catalyst which comprises a zeolite prepared by the process of controlled removal of aluminum from a crystalline aluminosilicate zeolite material which comprises:
(a) subjecting the zeolite material to a treatment whereby the pore system of the zeolite material is filled substantially completely with a foreign material;
(b) selectively removing a portion of said foreign material from an outer zone of the zeolite crystal structure;
(c) contacting the zeolite from step (b) with a dealuminating agent to which the said foreign material is substantially inert under the process conditions for a sufficient time and under suitable process conditions as to remove at least some of the aluminum from the zeolite; and
(d) subjecting the thus partially de-aluminated zeolite to further treatment whereby to remove substantially the remainder of said foreign material, said de-aluminated zeolite being further characterized as comprising an inner core having silica to alumina mole ratio substantially characteristic of the untreated zeolite and an outer skin which has been at least partially dealuminated and which has a higher silica to alumina mole ratio than said inner core.

2. A process according to claim 1 wherein the zeolite is from a crystalline aluminosilicate zeolite selected from the group consisting of mordenites, ferrierites, FU-1, FU-9, Nu-1, Nu-2, Nu-3, Nu-4, Nu-5, Nu-6, Nu-10, EU-1, EU-2, EU-4, ZSM-5, 11, 12, 35, 38 and 48.

3. A process according to claim 1 wherein the aluminosilicate zeolite is ZSM-5.

* * * * *